United States Patent
Hasse et al.

(10) Patent No.: US 8,028,385 B2
(45) Date of Patent: Oct. 4, 2011

(54) PATTERNED TAMPON AND METHOD OF MAKING

(75) Inventors: Margaret Henderson Hasse, Wyoming, OH (US); Daniel Raymond Wiegele, Cincinnati, OH (US); Robert Clark Avery, Jr., Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 874 days.

(21) Appl. No.: 11/860,655

(22) Filed: Sep. 25, 2007

(65) Prior Publication Data
US 2009/0082712 A1    Mar. 26, 2009

(51) Int. Cl.
*A61F 13/20*    (2006.01)
(52) U.S. Cl. .......................................................... 28/118
(58) Field of Classification Search ...................... 28/118, 28/119, 120, 122, 123; 604/385.17, 904, 604/385.18; 264/319, 324, 320, 334; 425/392, 425/394, 395
See application file for complete search history.

(56) References Cited

U.S. PATENT DOCUMENTS

| | | | |
|---|---|---|---|
| 1,997,467 A * | 4/1935 | Manley | ........................ 433/136 |
| 2,123,750 A | 7/1938 | Schulz | |
| 2,499,414 A | 3/1950 | Rabell | |
| 3,428,044 A | 2/1969 | Whitehead et al. | |
| 3,738,364 A | 6/1973 | Brien et al. | |
| 3,854,481 A | 12/1974 | Messing | |
| 3,946,737 A | 3/1976 | Kobler | |
| 4,175,561 A | 11/1979 | Hirschman | |
| 4,326,527 A | 4/1982 | Wollangk et al. | |
| 4,335,720 A | 6/1982 | Glassman | |
| 4,591,523 A | 5/1986 | Thompson | |
| 4,609,518 A | 9/1986 | Curro et al. | |
| 4,629,643 A | 12/1986 | Curro et al. | |
| 4,685,178 A | 8/1987 | Nakanishi | |
| 4,705,514 A | 11/1987 | Barnard | |
| 4,839,216 A | 6/1989 | Curro et al. | |
| 4,951,368 A | 8/1990 | Heinen | |
| 5,153,971 A | 10/1992 | Van Iten | |
| 5,350,371 A | 9/1994 | Van Iten | |
| 5,592,725 A | 1/1997 | Brinker | |
| 5,718,675 A | 2/1998 | Leijd | |
| 5,788,910 A | 8/1998 | McNeilis et al. | |
| 5,832,576 A | 11/1998 | Leutwyler et al. | |
| 5,891,081 A | 4/1999 | McNelis et al. | |

(Continued)

FOREIGN PATENT DOCUMENTS

DE   10 2005 0505514 A1    4/2007

(Continued)

OTHER PUBLICATIONS

U.S. Appl. No. 11/799,914, filed May 3, 2007, Gilbert et al.

(Continued)

*Primary Examiner* — Amy Vanatta
(74) *Attorney, Agent, or Firm* — Megan C. Hymore; James E. Oehlenschlager

(57) ABSTRACT

A tampon including a compressed pledget of absorbent material. The tampon has a body portion and a longitudinal axis, wherein the tampon includes at least one patterned impression with one or more design elements oriented substantially perpendicular to the longitudinal axis, wherein at least one design element is formed by contact with at least one corresponding pattern including at least one lead in portion. A method and apparatus for making the tampon are also disclosed.

6 Claims, 14 Drawing Sheets

U.S. PATENT DOCUMENTS

| | | | |
|---|---|---|---|
| 5,911,712 A | 6/1999 | Leutwyler et al. | |
| 5,958,321 A | 9/1999 | Schoelling et al. | |
| 6,003,216 A | 12/1999 | Hull, Jr. et al. | |
| 6,071,259 A | 6/2000 | Steiger et al. | |
| 6,090,038 A | 7/2000 | Zunker et al. | |
| 6,142,928 A | 11/2000 | Zunker et al. | |
| 6,156,021 A | 12/2000 | Tojkander | |
| 6,191,341 B1 * | 2/2001 | Shippert | 604/383 |
| 6,283,952 B1 | 9/2001 | Child et al. | |
| 6,310,269 B1 | 10/2001 | Friese et al. | |
| 6,450,985 B1 | 9/2002 | Schoelling et al. | |
| 6,719,743 B1 | 4/2004 | Wada | |
| 6,814,722 B2 | 11/2004 | Jackson et al. | |
| 6,824,536 B2 * | 11/2004 | Randall et al. | 604/385.18 |
| 6,889,409 B2 | 5/2005 | Friese et al. | |
| 6,932,805 B2 | 8/2005 | Kollwitz et al. | |
| 7,047,608 B2 * | 5/2006 | Sageser et al. | 28/118 |
| 7,059,026 B2 | 6/2006 | Friese et al. | |
| 7,060,057 B2 * | 6/2006 | Policappelli | 604/385.12 |
| 7,070,585 B2 | 7/2006 | Jensen | |
| 7,087,045 B2 | 8/2006 | Jensen | |
| 7,097,638 B2 | 8/2006 | Jensen | |
| 7,214,218 B2 * | 5/2007 | Carlin | 604/385.17 |
| 7,735,203 B2 * | 6/2010 | Stan et al. | 28/118 |
| 7,740,787 B2 * | 6/2010 | Hubbard et al. | 264/313 |
| 2001/0014348 A1 * | 8/2001 | Schoelling | 424/431 |
| 2002/0120243 A1 | 8/2002 | Kraemer et al. | |
| 2002/0151859 A1 | 10/2002 | Schoelling | |
| 2002/0157222 A1 | 10/2002 | Friese et al. | |
| 2003/0167048 A1 * | 9/2003 | Policappelli | 604/385.17 |
| 2004/0030280 A1 * | 2/2004 | Mercier | 604/11 |
| 2004/0030316 A1 | 2/2004 | Gubernick et al. | |
| 2004/0193131 A1 | 9/2004 | Wada | |
| 2004/0199137 A1 | 10/2004 | Lamb | |
| 2004/0244165 A1 * | 12/2004 | Bittner et al. | 28/118 |
| 2005/0059944 A1 | 3/2005 | Jackson et al. | |
| 2005/0080393 A1 * | 4/2005 | Policappelli | 604/385.18 |
| 2005/0096619 A1 | 5/2005 | Costa | |
| 2005/0113780 A1 * | 5/2005 | Gatto et al. | 604/385.17 |
| 2005/0113782 A1 * | 5/2005 | Carlin | 604/385.18 |
| 2005/0113783 A1 | 5/2005 | Carlin et al. | |
| 2005/0113786 A1 | 5/2005 | Carlin | |
| 2005/0113787 A1 * | 5/2005 | Carlin | 604/385.18 |
| 2005/0113788 A1 | 5/2005 | Carlin | |
| 2005/0113807 A1 | 5/2005 | Carlin | |
| 2005/0193536 A1 | 9/2005 | Ingelgem et al. | |
| 2005/0251979 A1 | 11/2005 | Friese et al. | |
| 2006/0185136 A1 | 8/2006 | Friese et al. | |
| 2007/0083182 A1 | 4/2007 | Schoelling | |
| 2008/0119811 A1 * | 5/2008 | Gilbert et al. | 604/385.17 |
| 2008/0275411 A1 | 11/2008 | Hughes et al. | |
| 2008/0275417 A1 * | 11/2008 | Gilbert et al. | 604/385.18 |
| 2008/0275418 A1 | 11/2008 | Hughes et al. | |
| 2010/0298756 A1 | 11/2010 | Hughes et al. | |

FOREIGN PATENT DOCUMENTS

| | | |
|---|---|---|
| WO | WO 2006/077091 A1 | 7/2006 |
| WO | WO 2007/088057 A1 | 8/2007 |

OTHER PUBLICATIONS

U.S. Appl. No. 11/601,946, filed Nov. 20, 2006, Gilbert et al.
U.S. Appl. No. 11/504,983, filed Aug. 16, 2006, Gilbert et al.
U.S. Appl. No. 11/595,322, filed Nov. 10, 2006, Gilbert et al.
U.S. Appl. No. 11/860,614, filed Sep. 25, 2007, Gilbert.
PCT International Search Report dated Dec. 6, 2009.

* cited by examiner

PATTERNED TAMPON AND METHOD OF MAKING

FIELD OF THE INVENTION

The invention relates to improved tampons and to apparatuses and methods of making such tampons.

BACKGROUND OF THE INVENTION

Tampons are generally compressed absorbent structures typically shaped and sized to fit into a body cavity, such as, for example a human vagina. Often, due to the processes used for making tampons, the outer surface of the tampon, including the outer surface of the insertion end, the withdrawal end and/or the main body, may be relatively rough, uneven, crenulated, and unattractive. Such characteristics in the surface topography of a tampon may provide the user with a negative impression of the product, especially when seen prior to use. For example, the insertion end of a tampon is often visible to a user prior to application, such as, e.g., with a digital tampon and/or a tampon provided in an applicator that at least partially displays the outer surface of the tampon. Furthermore, surface topography of tampons, such as, e.g., the insertion end, may affect tampon performance, such as, for example, fluid absorption characteristics and/or user comfort during insertion.

Accordingly, it may be desirable to provide tampons that have a relatively attractive surface, such as the insertion end, withdrawal end and/or main body, prior to use. In addition, it may be advantageous to have a tampon with one or more portions with improved fluid absorption characteristics. Further, it may be desirable to provide a tampon that is more comfortable for the user to insert. Further still, it would be desirable to provide an apparatus and/or method of making a tampon that provides a tampon with at least one relatively appealing portions. It would also be desirable to provide a tampon that is more comfortable for the user to insert. Moreover, it would be desirable to provide a tampon with improved absorption properties during use.

SUMMARY OF THE INVENTION

Embodiments of the invention address the foregoing and encompass a tampon which may comprise a compressed pledget of absorbent material. The tampon may have a body portion and a longitudinal axis, wherein the tampon may include at least one patterned impression with one or more design elements oriented substantially perpendicular to the longitudinal axis. The compressed pledget may have been compressed into a tampon mold having a mold cavity for receiving the compressed pledget of absorbent material, wherein the tampon mold may include at least one pattern oriented substantially perpendicular to the longitudinal axis of the compressed pledget, wherein the at least one pattern may include at least one smooth lead in portion to one or more design elements.

According to another aspect of this invention, an apparatus for making a tampon is provided and may include a compression machine for receiving and compressing an uncompressed pledget of absorbent material so as to form a compressed pledget. The apparatus may also include a tampon mold having a mold cavity for receiving the compressed pledget of absorbent material, wherein the tampon mold may include at least one pattern oriented substantially perpendicular to the longitudinal axis of the compressed pledget, wherein the at least one pattern may include at least one lead in portion to one or more design elements. Furthermore, the apparatus may include a compression member for pushing the compressed pledget into the tampon mold cavity.

According to yet another aspect of this invention, a method is provided for making a tampon which may include providing an uncompressed pledget of absorbent material, and compressing the uncompressed pledget in a compression machine. The method may also include feeding the compressed pledget with a compression member into a tampon mold having a mold cavity for receiving the compressed pledget of absorbent material, wherein the mold cavity may include at least one pattern oriented substantially perpendicular to the longitudinal axis of the compressed pledget, and wherein the at least one pattern may include at least one smooth lead in portion associated with one or more design elements.

Other embodiments, aspects, features, and advantages of the invention may be apparent from reading the following detailed description, drawings, and claims.

DETAILED DESCRIPTION OF THE INVENTION

Figure 1:
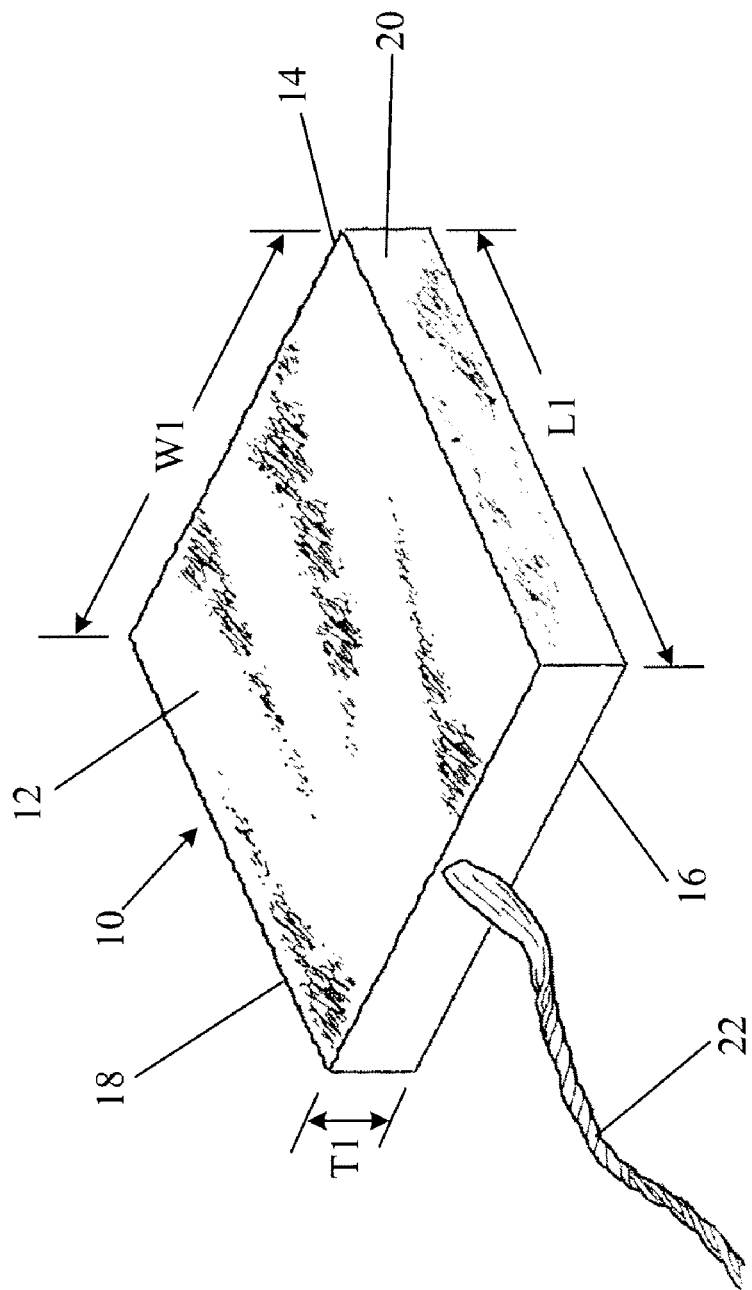
FIG. 1 is a perspective view of an uncompressed pledget of absorbent material for use in making a tampon in accordance with an embodiment of the present invention.
Figure 2:
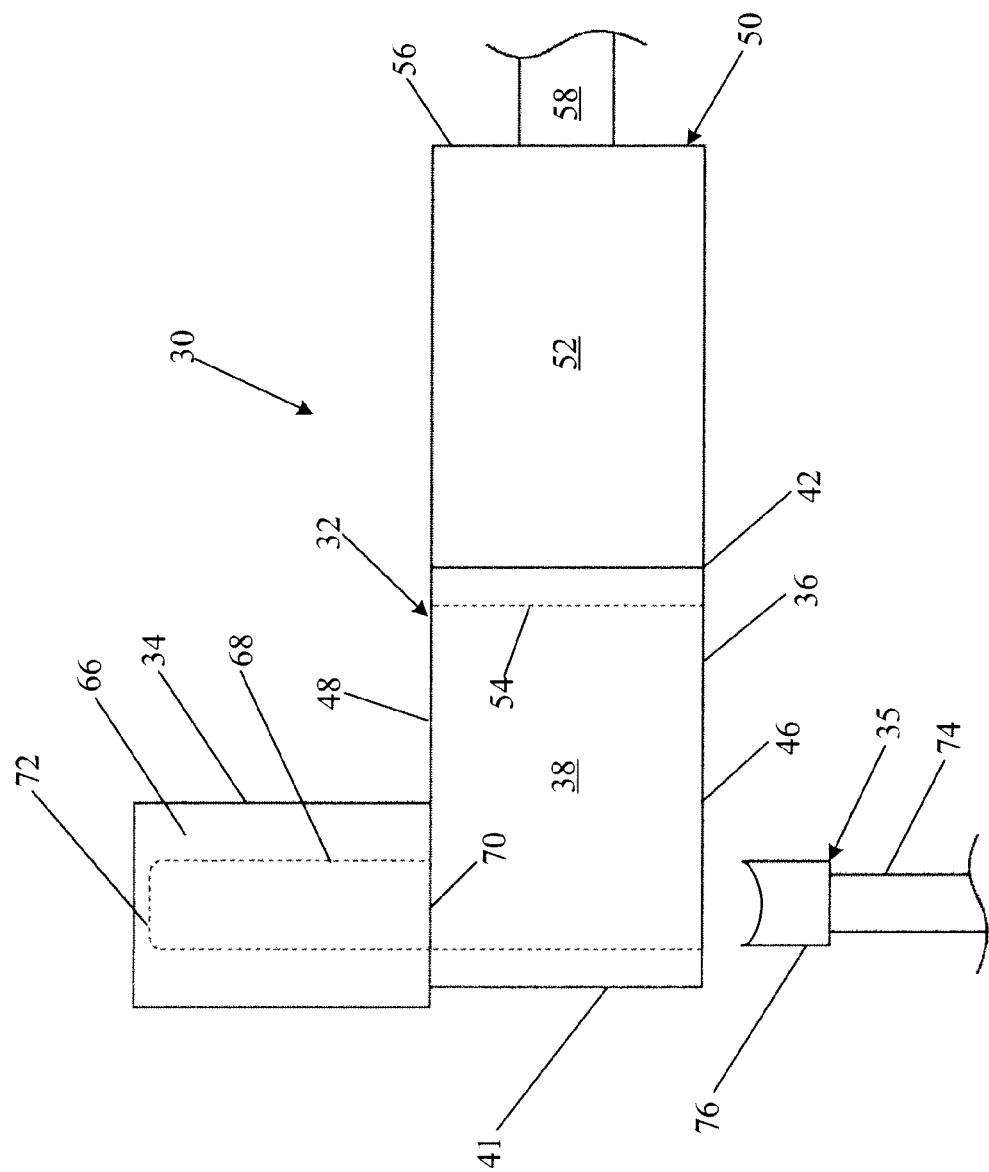
FIG. 2 is a plan view of a tampon forming apparatus, in accordance with an embodiment of the present invention, with the tampon compression machine in an open position.

As summarized above, this invention may encompass a tampon and an apparatus and method for making such a tampon. As will be explained in more detail below, tampons in accordance with embodiments of the invention may be made by compressing an uncompressed pledget of absorbent material with a tampon forming apparatus having a relatively smooth lead in portion to design elements so that patterned impressions substantially perpendicular to the longitudinal axis of the tampon can be formed in the surface of the tampon. Pushing the compressed pledget over the relatively smooth lead in portion in the longitudinal direction of the compressed pledget during compression in the direction of the pledget length may permit the material to avoid impinging against any relatively sharp surfaces. As a result, tampons made in accordance with certain embodiments of this invention may have an attractive surface appearance or improved re-expansion abilities, or both. Further, having a relatively smooth trailing or transition portion leading or trailing away from the pattern may aid pattern definition.

Section A below describes terms for assisting the reader in understanding features of the invention, but not introducing limitations in the terms inconsistent with the context with which they are used in the specification. Section B is a detailed description of the drawings illustrating an apparatus in accordance with embodiments of this invention. Section C describes methods of manufacturing tampons in accordance with embodiments of this invention and Section D describes tampons made in accordance with this invention.

A. Terms

As used herein, "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

As used herein, "mold" refers to a structure for shaping a pledget during compression and/or retaining the shape for a compressed pledget subsequent to compression during the stabilization process. Molds have an inner surface defining an inner cavity and an outer surface. The inner cavity is structured to define or mirror the shape of the compressed absorbent pledget. Thus, in some embodiments the pledget conforms to the shape of the inner cavity of the mold by a restraining force to result in a self-sustaining shape and is retained in the inner cavity during the stabilization process. The inner cavity may be profiled to achieve any shape known in the art including, but not limited to, cylindrical, oval, rectangular, triangular, trapezoidal, semi-circular, hourglass, serpentine or other suitable shapes. The outer surface of the mold is the surface external to the inner surface and can be profiled or shaped in any manner, such as, rectangular, cylindrical or oblong. The mold may comprise one or more members. Suitable molds used in embodiments of the invention may include, but may not be limited to unitary molds, comprising one member, and split cavity molds. Split cavity molds may be used when producing shaped tampons, such as those disclosed in U.S. patent application Ser. No. 10/150,050 entitled "Substantially Serpentine Shaped Tampon," and U.S. patent application Ser. No. 10/150,055, entitled "Shaped Tampon," both filed on Mar. 18, 2002.

As used herein the term "pledget" refers to a construction of absorbent material prior to the compression of such construction into a tampon.

As used herein, "self-sustaining" is a measure of the degree or sufficiency to which the tampon retains its compressed form after stabilization such that in the subsequent absence of external forces, the resulting tampon will tend to retain its vaginally insertable shape and size. It will be understood by one of skill in the art that this self-sustaining form need not, and may not persist during actual use of the tampon. That is, once the tampon is inserted into the vagina or other body cavity and begins to acquire fluid, the tampon will begin to expand and may lose its self-sustaining form.

The term "shaped tampons," as used herein, refers to compressed pledgets having either a substantially serpentine shape, an "undercut" or "waist," or a non-uniform cross-section traversing from the insertion end to the withdrawal end of the tampon. The phrase "substantially serpentine" refers to a non-linear dimension between any two points spaced at least about 5 mm apart. The term "undercut" refers to tampons having a protuberance or indentation that impedes the withdrawal from a unitary mold. For example, shaped tampons may be hourglass shaped having at least one perimeter in the center of the tampon or "waist" that is less than both an insertion end perimeter and a withdrawal end perimeter.

As used herein, the term "split cavity mold" is a mold comprised of two or more members that when brought together complete the inner cavity of the mold. Each member of the split cavity mold comprises at least a portion of the inner surface that when brought together or closed completes the mold structure. The split cavity mold is designed such that at least two or more of the mold members can be at least partially separated, if not fully separated, typically after the tampon has acquired a self-sustaining shape, to expand the cavity volume circumscribed by the inner surface(s) thus permitting the easier removal of the tampon from the mold. Partial separation can occur when only a portion of two mold members are separated while other portions of the two mold members remain in contact. Where each member's inner surface portion joins the inner surface portion of another member, those points of adjacency can define a straight line, a curve, or another seam of any convoluted intersection or seam of any regular or irregular form. The elements of the split cavity in some embodiments may be held in appropriate position relative to each other by linking elements of any form including bars, rods, linked cams, chains, cables, wires, wedges, screws, etc.

The term "stabilized," as used herein, refers to a tampon in a self-sustaining state wherein it has overcome the natural tendency to re-expand to the original size, shape and volume of the absorbent material and overwrap, which comprise the pledget.

As used herein the term "tampon," refers to any type of absorbent structure that is inserted into the vaginal canal or other body cavities for the absorption of fluid therefrom, to aid in wound healing, or for the delivery of active materials, such as medicaments, or moisture. The tampon may be compressed into a generally cylindrical configuration in the radial direction, axially along the longitudinal axis or in both the radial and axial directions. While the tampon may be compressed into a substantially cylindrical configuration, other shapes are possible. These may include shapes having a cross section that may be described as oval, rectangular, triangular, trapezoidal, semi-circular, hourglass, serpentine, or other suitable shapes. Tampons have an insertion end, withdrawal end, a length, a width, a longitudinal axis and a radial axis. The tampon's length can be measured from the insertion end to the withdrawal end along the longitudinal axis. A typical compressed tampon for human use is within a range from about 30 to about 60 mm in length. A tampon may be straight or non-linear in shape, such as curved along the longitudinal axis. A typical compressed tampon is within a range from about 8 to about 20 mm wide. The width of a tampon, unless otherwise stated in the specification, corresponds to the distance across the largest cross-section, along the length of the tampon and perpendicular to the longitudinal axis of the tampon.

The term "vaginal cavity," "within the vagina," and "vaginal interior," as used herein, are intended to be synonymous and refer to the internal genitalia of the mammalian female in the pudendal region of the body. The term "vaginal cavity" as used herein is intended to refer to the space located between the introitus of the vagina (sometimes referred to as the sphincter of the vagina or hymeneal ring,) and the cervix. The terms "vaginal cavity," "within the vagina" and "vaginal interior," do not include the interlabial space, the floor of vestibule or the externally visible genitalia.

As used herein, "cm" is centimeter, "g" is grams, "g/m$^2$" is grams per meter squared, "L" is liters, "L/s" is liters per second, "mL" is milliliters", "mm" is millimeters, "min" is minutes, "rpm" rate per minute, and "s" is seconds.

As used herein, the "tampon compression machine" is a machine assembly that includes parts that may compress a pledget. Typically a pledget compressed in the tampon compression machine is then transferred to a mold for final shaping into a self-sustaining form of a vaginally insertable shape where, the mold may further compress parts of the pledget beyond that which the tampon compression machine accomplished prior.

As used herein, the "compression member" is any member that can be used to compress a pledget. It can also function to transfer a compressed pledget.

As used herein, "actuating" is any force delivered by an electric motor, mechanical transmission, pneumatically, linear drive, manual, and/or hydraulic.

As used herein, a "high aspect ratio shape" is any shape in which the width is greater than the thickness of the shape. The shape may not necessarily contain any defined circles, arcs, or cross-sectional portions.

As used herein, a "pattern," "pattern structure," "pattern die element," or "pattern element" is a predefined shape formed in a mold that is capable of forming a corresponding patterned impression on a surface of a tampon pledget.

As used herein, a "base portion" is a portion of a mold without a pattern.

As used herein, a "lead in portion" is a portion of a mold immediately adjacent to a pattern associated with a mold and is on an opposing side of the pattern from a trailing portion. A "lead in portion" is generally the portion of the mold where a pledget enters the mold, however it is possible that a pledget can enter the mold at a "trailing portion" of the mold in accordance with certain embodiments of the invention.

As used herein, a "trailing portion" is a portion of a mold immediately adjacent to a pattern associated with a mold and is on an opposing side of the pattern from the lead in portion.

B. Tampons and Tampon Manufacturing Apparatus

Turning to FIG. 1, an uncompressed pledget 10 of absorbent material 12 is illustrated. The uncompressed pledget 10 may be compressed to form a tampon in accordance with an embodiment of this invention. The uncompressed pledget 10 extends from an insertion end 14 to a withdrawal end 16 with opposing sides 18 and 20 extending from the insertion end 14 to the withdrawal end 16. A withdrawal cord or drawstring 22 may be connected to and extend from the withdrawal end 16 of the uncompressed pledget 10.

Although the uncompressed pledget 10 is illustrated as having a generally square or rectangular shape, the uncompressed pledget 10 can have a variety of shapes including, but not limited to, oval, round, chevron, square, rectangular, and the like. The uncompressed pledget 10 may have a length L1 extending from the insertion end 14 to the withdrawal end 16 of the uncompressed pledget 10, a width W1 extending from the one side 18 of the uncompressed pledget 10 to the other side 20 and perpendicularly to the length L1, and a thickness T1 extending perpendicularly to both the length L1 and width W1 of the uncompressed pledget 10.

The absorbent material 12 of the uncompressed pledget 10 may be constructed from a wide variety of liquid absorbing materials commonly used in absorbent articles. Such materials include but are not limited to rayon (such as GALAXY rayon, SARILLE L rayon both available from Accordis Kelheim GmbH of Kelheim, Germany), cotton, folded tissues, woven materials, nonwoven webs, synthetic and/or natural fibers or sheathing, comminuted wood pulp which is generally referred to as airfelt, or combinations of these materials. Other materials that may be incorporated into the pledget 10 include peat moss, absorbent foams (such as those disclosed in U.S. Pat. No. 3,994,298 issued to Desmarais on Nov. 30, 1976 and U.S. Pat. No. 5,795,921 issued to Dyer, et al.), capillary channel fibers (such as those disclosed in U.S. Pat. No. 5,356,405 issued to Thompson, et al. issued on Oct. 18, 1994), high capacity fibers (such as those disclosed U.S. Pat. No. 4,044,766 issued to Kaczmarck, et al. on Aug. 30, 1994), and super absorbent polymers or absorbent gelling materials (such as those disclosed in U.S. Pat. No. 5,830,543 issued to Miyake, et al. on Nov. 3, 1998). A more detailed description of liquid absorbing materials shapes and dimensions can be found in U.S. Pat. No. 6,740,070 to Raymond Agyapong.

The uncompressed pledget 10 may optionally include an overwrap comprising materials such as rayon, cotton, bicomponent fibers, polyethylene, polypropylene, other suitable natural or synthetic fibers known in the art, and mixtures thereof In some embodiments, the uncompressed pledget 10 has a nonwoven overwrap comprised of bicomponent fibers that have a polypropylene core surrounded by polyethylene manufactured by Vliesstoffwerke Christian Heinrich Sandler GmbH and Company KG (Schwarzenbach/Salle Germany) under the trade name SAS B31812000. In other embodiments, the tampon may comprise a nonwoven overwrap of a hydro entangled blend of 50% rayon, 50% polyester available as BBA 140027 produced by BBA Corporation of South Carolina, US. The overwraps may be treated to hydrophilic, hydrophobic, wicking or nonwicking.

The uncompressed pledget 10 may optionally include a secondary absorbent member, an additional overwrap, a skirt portion and/or an applicator. A withdrawal cord 22 may be attached to the uncompressed pledget 10 and may be made of any suitable material in the prior art such as cotton and rayon. U.S. Pat. No. 6,258,075 issued to Taylor et al. describes a variety of secondary absorbent members for use in pledgets. An example of a skirt portion is disclosed in U.S. Pat. No. 6,840,927 to Margaret Hasse.

A tampon forming apparatus 30 for making tampons in accordance with an embodiment of this invention is illustrated in FIGS. 2-9. The tampon forming apparatus 30 may generally comprise a tampon compression machine 32 for initially compressing the uncompressed pledget 10 of absorbent material to form a compressed pledget 33, a mold 34 (in this case shown as a split cavity mold) for receiving the compressed pledget 33 and setting the compressed pledget 33 in a self-sustaining shape, and a compression member 35 for pushing the compressed pledget 33 into the split cavity mold 34. In other embodiments, other types of molds such as a unitary or single piece mold can be used instead of a split cavity mold.

Figure 3:
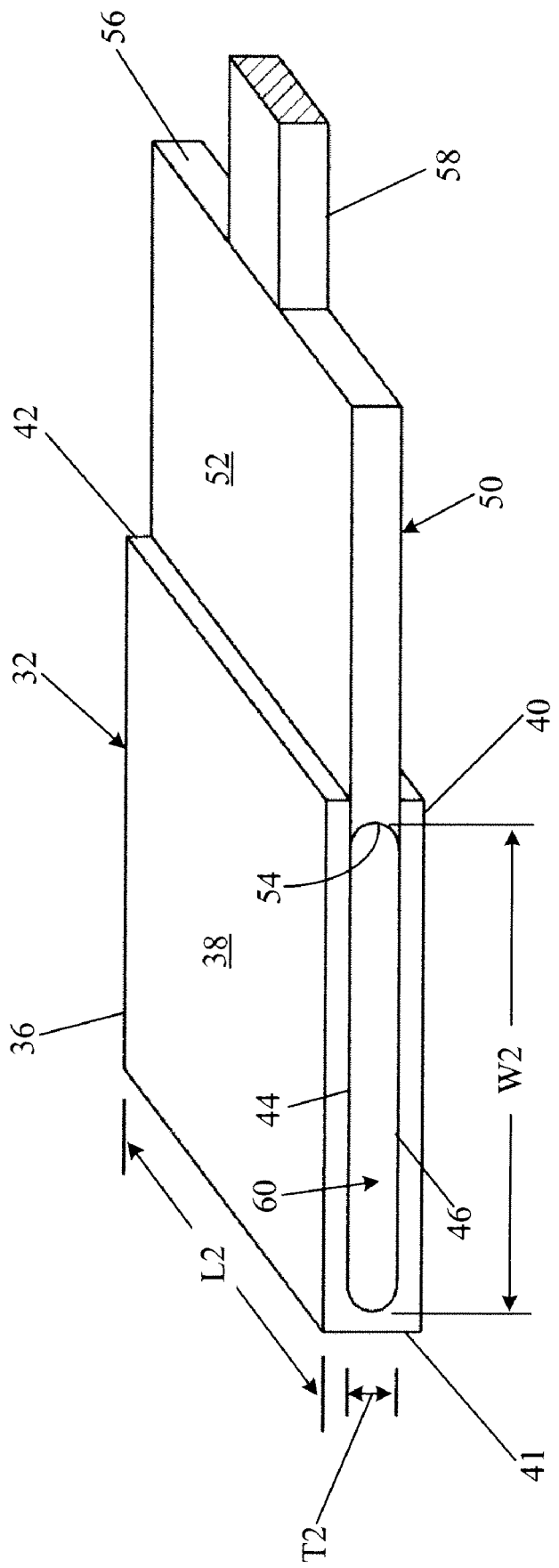
FIG. 3 is a perspective view of the tampon compression machine of FIG. 2 in an open position.
Figure 4:
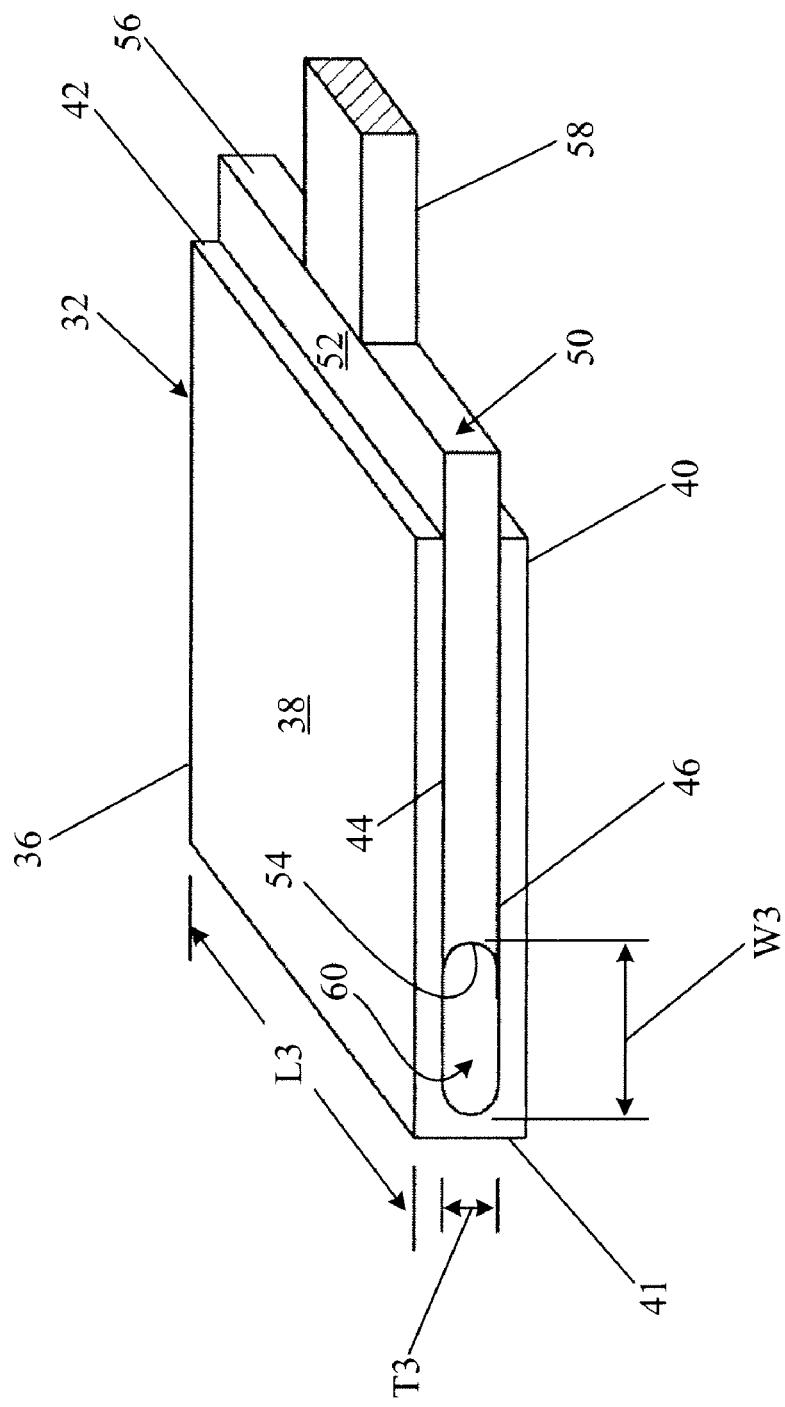
FIG. 4 is a perspective view of the tampon compression machine of FIG. 2 in a compression position.

The tampon compression machine 32 may comprise a u-shaped anvil 36, best shown in FIGS. 3 and 4. The tampon compression machine 32 may comprise a top plate 38 and a juxtaposed bottom plate 40 extending from an end wall 41 connecting the top and bottom plates 38 and 40 to an open end 42 thereby forming a channel 44 between the top and bottom plates 38 and 40. The channel 44 may extend from an inlet end 46 to a discharge end 48 of the anvil 36. The tampon compression machine 32 may also comprise a die 50 comprising a solid plate 52 extending from a leading end 54 to a trailing end 56 and an actuating rod 58 connected to the trailing end 56 for reciprocating the die 50 within the channel 44 of the anvil 36. The leading end 54 of the die 50 and the top and bottom plates 38 and 40 and end wall 41 of the anvil 36 may form a compression machine cavity 60 within the channel 44 of the anvil 36 for receiving the uncompressed pledget 10. The die 50 may compress the uncompressed pledget 10 in the compression machine cavity to form the compressed pledget 33.

In certain embodiments, opposing plates 38 and 40 with end walls on opposing ends may move relative to each other and thereby compress the uncompressed pledget 10. Other configurations for the compression machine 32 for carrying out the functions described herein will be apparent to those skilled in the art from reading the details of this specification.

The compression machine cavity 60 of the tampon compression machine 32 may have an oval cross sectional shape as illustrated in FIGS. 3 and 4, but it should be understood that the compression machine cavity 60 may have other shapes as well including, but not limited to, round, square, and rectangular cross-sectional shapes. When in an open configuration as illustrated in FIG. 3, the compression machine cavity 60 may have a length L2 extending from the inlet end 46 of the anvil 36 of the discharge end 48, a width W2 extending from the interior of the anvil end wall 41 to the leading end 54 of the die 50 and perpendicular to the length L2, and a thickness T2 extending from the interior of the top plate 38 of the anvil 36 to the bottom plate 40 perpendicular both to the length L2 and width W2 of the compression machine cavity 60. In some embodiments, the width W2 of the compression machine cavity 60 when the compression machine cavity is in an open configuration may be close to or greater than the width W2 of the uncompressed pledget 10. In certain embodiments, the length L2 of the compression machine cavity 60 may also be close to or greater than the length L1 of the uncompressed pledget 10.

When in a compression configuration as illustrated in FIG. 4, the compression machine cavity 60 may have a length L3 which is the same as the length L2 in the open configuration and a thickness T3 which is same thickness as T2 in the open configuration, but may have a width W3 which may be substantially less than the width W2 of the compression machine cavity 60 in the open configuration and may be substantially less than the width W1 of the uncompressed pledget 10. In certain embodiments when the uncompressed pledget 10 is compressed in the tampon compression machine 32, the compressed pledget 33 may adopt the cross-sectional shape and width and thickness of the compression machine cavity 60 in the compressed configuration. Thus, the compressed pledget 33 may have a width of W3 and a thickness of T3. The manner of actuation of the die 50 within the anvil channel 44 to compress the pledget 10 may be by any suitable means to drive the actuating rod 58.

The degree of compression of the uncompressed pledget 10 in the compression machine cavity 60 in the widthwise direction may be a major component of the compression. In accordance with certain embodiments of this invention, the major compression of the uncompressed pledget in the compression machine cavity 60 in the widthwise direction is within a range from about 65% to about 90% of the original width of the uncompressed pledget 10. The degree of compression of the uncompressed pledget 10 in the thickness and lengthwise directions may be a minor component of the compression and, in accordance with certain embodiments of this invention, the minor compression of the uncompressed pledget 10 in the compression machine cavity 60 in the thickness and lengthwise directions may be no more than about 40% of the original width of the uncompressed pledget 10. In accordance with certain embodiments of this invention, the major compression of the uncompressed pledget 10 in the compression machine cavity 60 in the widthwise direction may be from about 75% to about 85% of the original width of the uncompressed pledget 10 and the minor compression of the uncompressed pledget 10 in the compression machine cavity 60 in the thickness and lengthwise directions may be no more than about 30% of the original width of the uncompressed pledget 10. It should be understood that it is contemplated in certain embodiments of the invention that there may be no compression of the uncompressed pledget 10 in the lengthwise and/or thickness directions.

Figure 6:
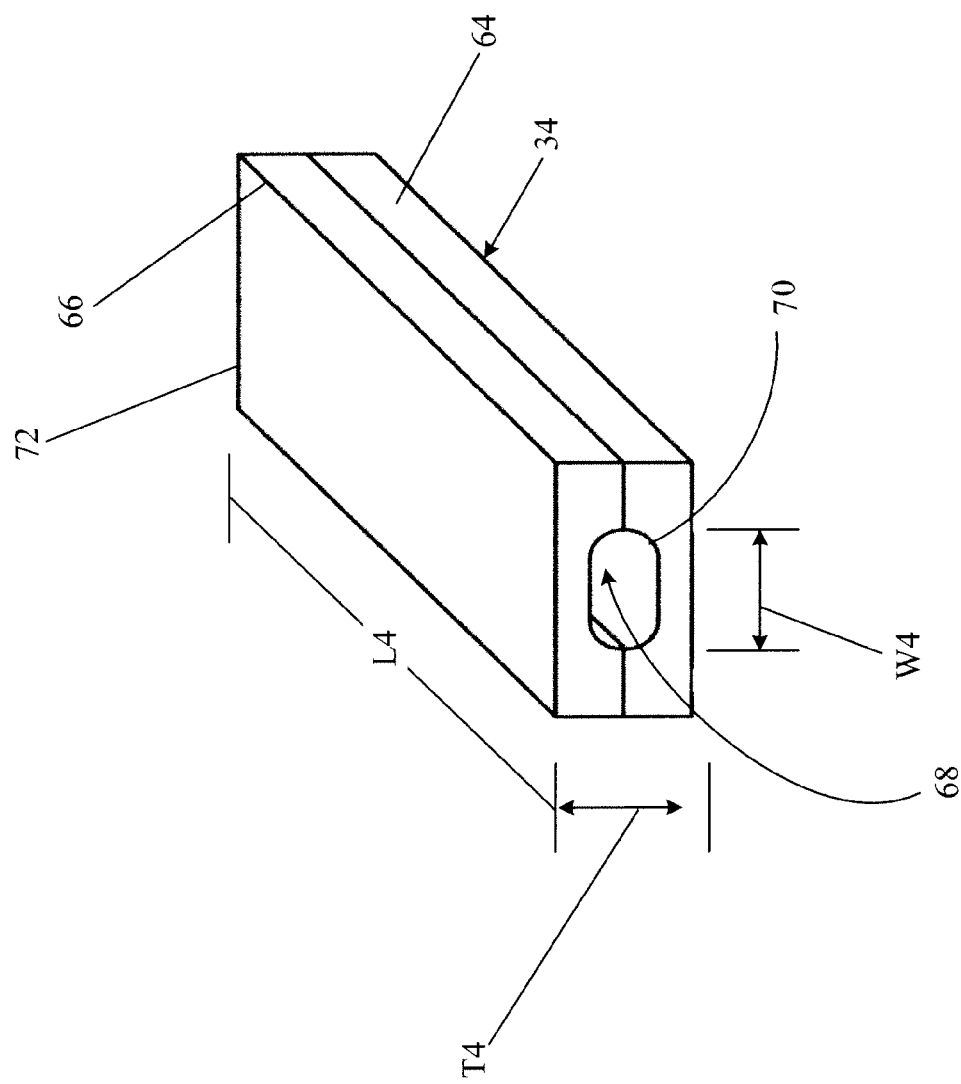
FIG. 6 is a perspective view of a split cavity tampon mold which is part of the tampon forming apparatus illustrated in FIG. 2.
Figure 7:
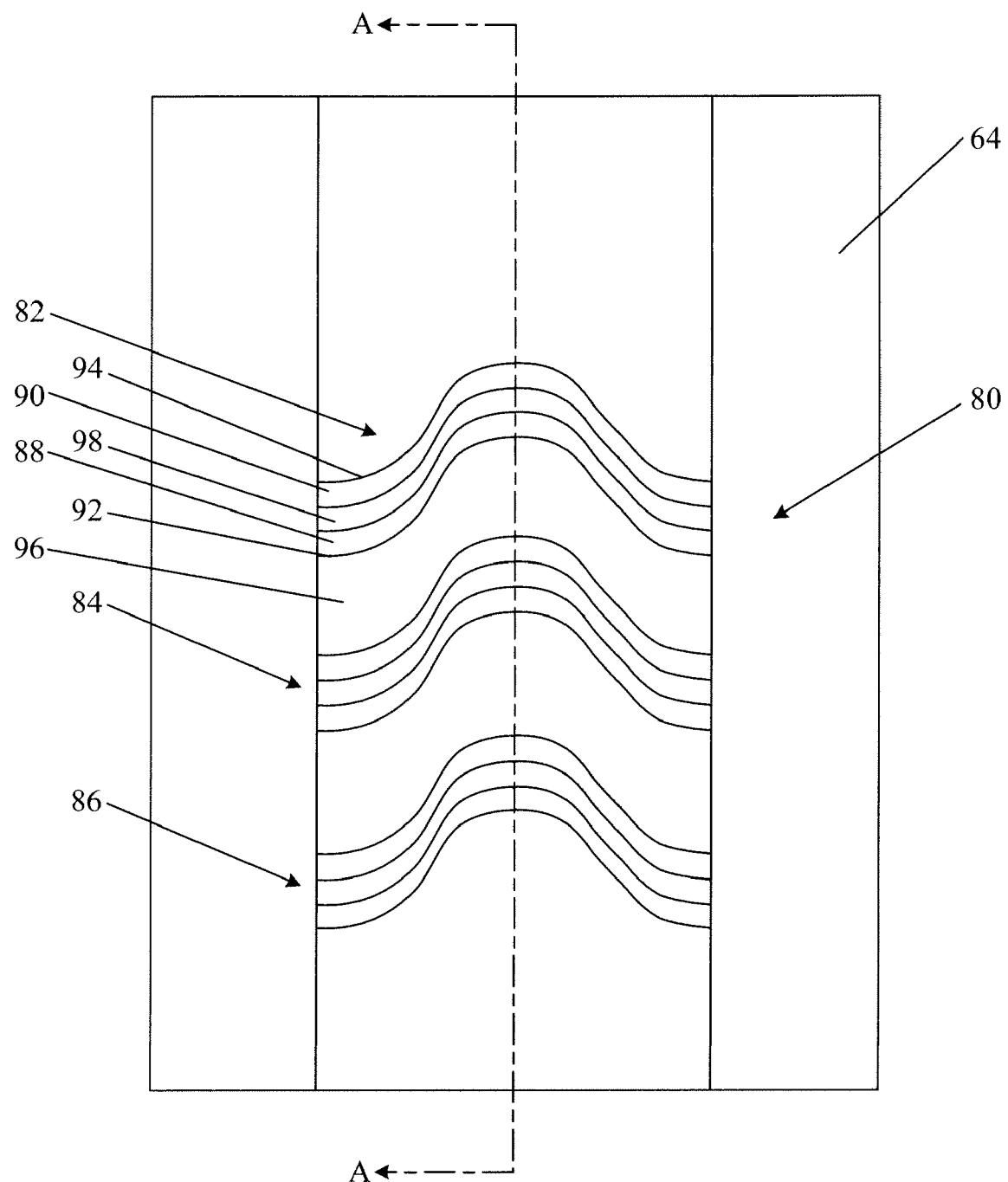
FIG. 7 is an upper view of a tampon split mold cavity in accordance with an embodiment of the invention.
Figure 8:
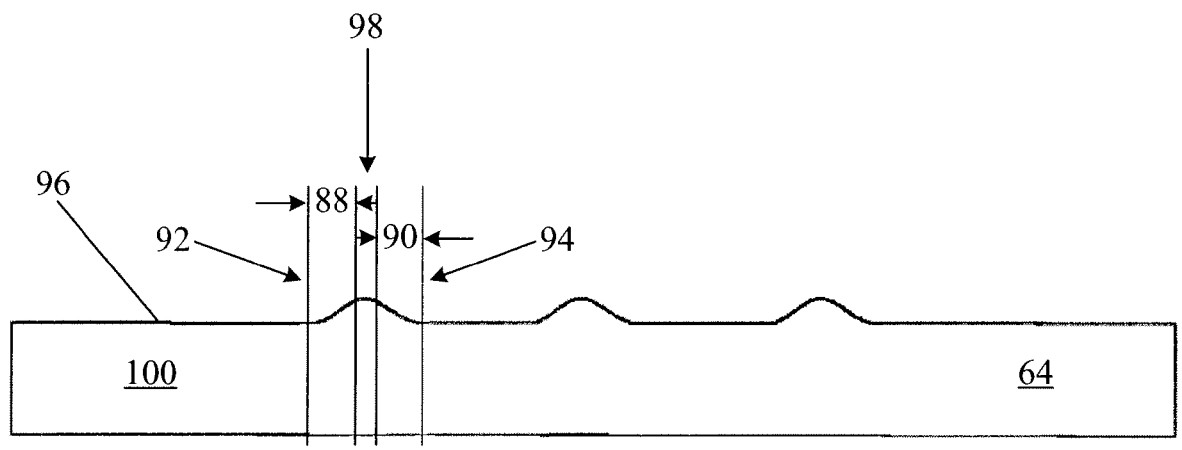
FIG. 8 is a lower cross-sectional view of the tampon split mold cavity in FIG. 7.
Figure 9:
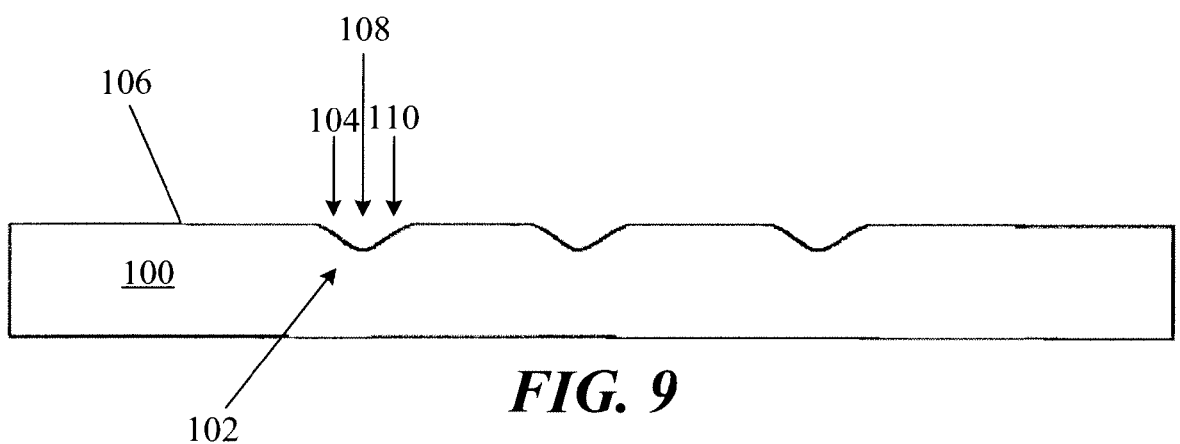
FIG. 9 is a lower cross-sectional view of another example tampon split mold cavity in accordance with an embodiment of the invention.

As shown in FIG. 6, the mold 34, in this case a split cavity mold, may generally comprise a first half cavity mold plate 64 and a second half cavity mold plate 66 which, when joined together in juxtaposed fashion, form the split cavity mold 34 with a mold cavity 68 extending from an inlet end 70 of the mold 34 to a distal end 72 of the mold 34. Although a split cavity mold 34 is illustrated in FIG. 6, it should be understood that other types of mold structures may be used as well. Examples of a split mold cavity with an associated first half cavity mold plate and a second half cavity mold plate are illustrated in FIGS. 7-9 described in greater detail below. Split cavity mold structures are disclosed in detail U.S. Pat. No. 7,047,608 to Sageser, et al. and pending U.S. patent application Ser. No. 10/887,645 entitled "Compressed, Gas Stabilized Tampon Having Multiple Folds" filed on Jul. 9, 2004.

The mold cavity 68 of the mold 34 may generally have a cross-sectional shape similar to the cross-sectional shape of the compression machine cavity 60 when in the compressed configuration. Furthermore, the mold cavity 68 may have a length L4 extending from the inlet end 70 to a distal end 72 of the mold cavity, a width W4 extending substantially perpendicularly to the mold cavity length L4, and a thickness T4 extending substantially perpendicularly to both the length L4 and width W4 of the mold cavity 68. In certain embodiments, the width W4 and thickness T4 of the mold cavity 68 may be close to the width W3 and thickness T3 of the compression machine cavity 60 when in the compressed configuration. Because cross-sectional shape and dimensions of the compression machine cavity 60 and the compressed configuration are very similar to the cross-sectional shape and dimensions of the mold cavity 68, the compressed pledget 33 may not expand or otherwise change shape significantly when inserted directly from the compression machine cavity 60 into the mold cavity 68.

In certain embodiments, the mold 34 may include one or more patterns or pattern die elements with at least one design element including at least one lead in portion to the at least one design element, which may form corresponding patterned impressions on the exterior surface of a compressed pledget. Examples of patterns, pattern die elements, and design elements which may be associated with a mold 34 are described with respect to FIGS. 7-9.

Figure 5:
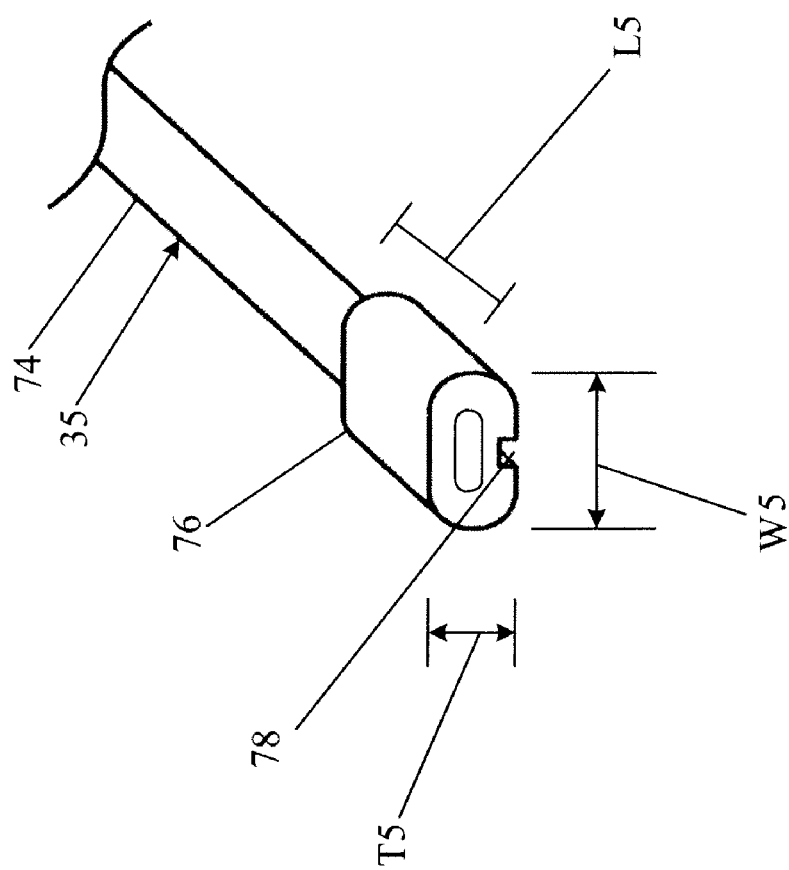
FIG. 5 is a partial perspective view of the compression member which forms part of the tampon forming apparatus in FIG. 2.

As shown in FIG. 5, the compression member 35 may comprise an actuating rod 74 and a head 76 connected to the actuating rod 74 for contacting the compressed pledget 33 to push the compressed pledget 33 from the compression machine cavity 60 into the mold cavity 68. The cross-sectional shape of the compression member head 76 may be similar to and, in certain embodiments, substantially identical to the cross-sectional shape of the compression machine cavity 60 in the compressed configuration and the cross-sectional configuration of the mold cavity 68. In certain embodiments, the compression member head 76 may have a width W5 and a thickness T5 extending perpendicularly to the head width. In certain embodiments, the compression member head 76 may have another geometry, configuration, or shape. For example, a compression member head, such as 76, may have a contoured shape with a pattern for impressing a corresponding contoured shape and patterned impression in a portion of the compressed pledget, such as 33.

The compression member head 76 may have a slot 78 therein for receiving the withdrawal cord 22 of the compressed pledget 33 so that the withdrawal cord is not cut by the compression member head 76 when the compression member head 76 transfers the compressed pledget 33 into the mold cavity 68.

FIG. 7 is an upper view of an example tampon split mold cavity for a split cavity mold in accordance with an embodiment of the invention. In the embodiment shown in FIG. 7, a first half cavity mold plate 64 may include one or more patterns or pattern die elements 80 for forming concave-shaped pattern impressions. The patterns or pattern die elements 80 in this example may be convex-shaped, and may include a series of three similarly shaped chevron-shaped pattern die elements 82 84, 86 oriented substantially or nearly perpendicular to the longitudinal axis of the split cavity mold or associated first half cavity mold plate. The chevron-shaped pattern die elements 82, 84, 86 may provide corresponding chevron-shaped patterned impressions oriented substantially or nearly perpendicular to the longitudinal axis of the compressed pledget, such as 33, after the compressed pledget becomes in substantial contact with the pattern die elements 82, 84, 86. Generally, a suitable pattern or pattern die element may include at least one design element oriented substantially or nearly perpendicular to the longitudinal axis of the mold or associated first or second half cavity mold plate, if in a split cavity mold. In other embodiments, suitable patterns or pattern die elements may include, but is not limited to, convex or concave-shaped elements, combinations of convex and concave-shaped elements, lines, chevrons, rain drops, peanuts, waves, dimples, concentric circles, cross-hatching, stars, polygons, triangles, rings, lines, rectangles, petals, ellipsoids, tear drops, letters, or waves.

Each of the patterns or pattern die elements 82, 84, 86 may include a lead in portion 88 and a trailing portion 90. The lead in portion 88 may be adjacent to a leading edge 92 of each of the pattern die elements 82, 84, 86, and the trailing portion 90 may be adjacent to a trailing edge 94 of the pattern die elements 82, 84, 86. As shown in the lower cross-sectional view of the first half cavity mold plate 64 in FIG. 8, the lead in portion 88 may be a relatively smooth surface that connects between a base portion 96 of the plate 64 and a raised portion 98 of the pattern die element 82, 84, 86. Likewise, the trailing portion 90 may be a relatively smooth surface that connects between a raised portion 98 of the pattern die element 82, 84, 86 and a base portion 96 of the plate 64.

FIG. 9 illustrates a lower cross-sectional view of a cavity mold plate 100 with a pattern or pattern die element 102 for forming a convex-shaped pattern impression. In this embodiment, the lead in portion 104 may be a relatively smooth surface that connects between a base portion 106 of the plate 100 and a depressed portion 108 of the pattern die element 102. Likewise, the trailing portion 110 may be a relatively smooth surface that connects between the depressed portion 108 of the pattern die element 102 and a base portion 106 of the plate 100.

In the embodiment of FIG. 8, the lead in portion 88 of the pattern die elements 82, 84, 86 may be approximately 0.7 mm in length, the raised portion 98 may be approximately 0.5 mm in height as measured from the base portion 96 of the plate 64, and the trailing portion 90 may be approximately 0.7 mm in length. In certain embodiments, a raised or depressed portion may be range between approximately 0.25 mm to approximately 4.0 mm in height with corresponding proportional changes to the lengths of the lead in portion and trailing portion associated with the pattern or patterned die element. In certain embodiments, the length of the lead in portion may be approximately 1 to 3 times the height of the pattern die element. That is, if the height of a lead in portion is approximately 1.0 mm, the length of the lead in portion may be between approximately 1.0 to approximately 3.0 mm in length. In certain embodiments, the lead in portion and trailing portion need not be the same length.

Generally, a suitable lead in portion may be a relatively smooth surface that slopes upward or downward from a base portion of an associated cavity mold plate to a raised or depressed portion of the plate. Likewise, a suitable trailing portion may be a relatively smooth surface that slopes upward or downward from a raised or depressed portion of an associated cavity mold plate to a base portion of the plate. In any instance, a suitable lead in portion and trailing portion for a pattern or pattern die element may provide a relatively smooth transition between a base portion of the associated plate and a raised or depressed portion of the pattern or pattern die element. Note that the cavity mold plate 100 shown in FIGS. 7-9 is shown by way of example and may not be to scale.

In one exemplary use of a split cavity mold, the first half cavity mold plate 64 may be used in conjunction with a second half cavity mold plate 66. When mounted together, the two plates 64, 66 may form a split cavity mold 34 for receiving a compressed pledget of absorbent material. In one embodiment, a second half cavity mold plate may include one or more patterns or pattern die elements, similar to pattern die elements 80, and such patterns or pattern die elements may be opposite or offset from the patterns or pattern die elements 80 associated with a first half cavity mold plate. In another embodiment, a second half cavity mold plate may include different shaped patterns or pattern die elements than the patterns or pattern die elements associated with a first half cavity mold plate. In yet another embodiment, a first half cavity mold plate may include one or more patterns or pattern die elements that may intersect or otherwise coordinate with one or more patterns or pattern die elements associated with a second half cavity mold plate.

In any instance, when a compressed pledget, such as 33, is introduced between the first half cavity mold plate 64 and the second half cavity mold plate 66, or the split cavity mold 34, the pledget material may initially flow over the base portion 96 of the plate 64. As noted above, other types of molds such as a unitary or single piece mold can be used instead of a split cavity mold. When the pledget material encounters the lead in portion 88, the pledget material may flow over the lead in portion 88 to the raised portion of the plate 66. The relatively smooth slope of the lead in portion 88 may assist the pledget material in moving across the surface of the split cavity mold 34 between the base portion 96 and the raised portion 98 with minimal tearing or damage to the pledget material. The pledget material may then flow over the raised portion of the plate 66 to the trailing portion 90, and flow over the trailing portion 90 to the lower portion 96 of the plate 64. The relatively smooth slope of the trailing portion 90 may assist the pledget material in moving across the surface of the mold 34 between the raised portion 98 and the base portion 96 with minimal or no tearing or damage to the pledget material. In this manner, a compressed pledget may be introduced into and pushed through the split cavity mold to facilitate formation of various pattern impressions which may be oriented substantially or nearly perpendicular to the longitudinal axis of the compressed pledget with minimal or no tearing or damage to the pledget material or compressed pledget. An example of the movement of the pledget material with respect to example cavity mold plates is shown and described in detail in FIG. 13.

Figure 16:
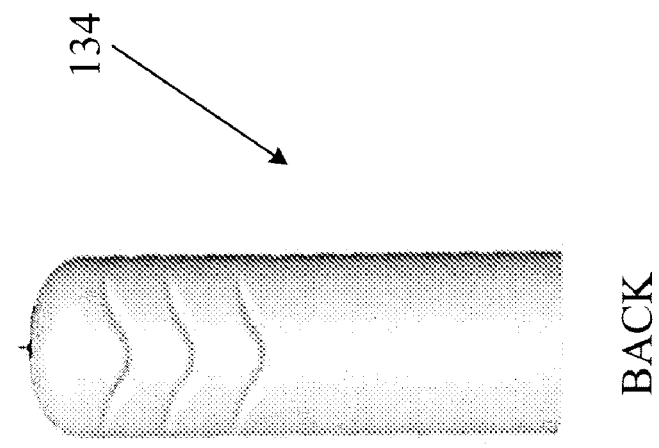
FIGS. 14-16 are perspective views of example tampons made in accordance with various embodiments of the invention.
Figure 15:
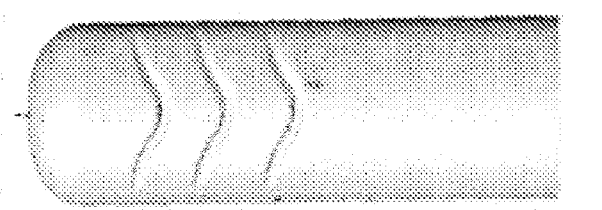
Figure 14:
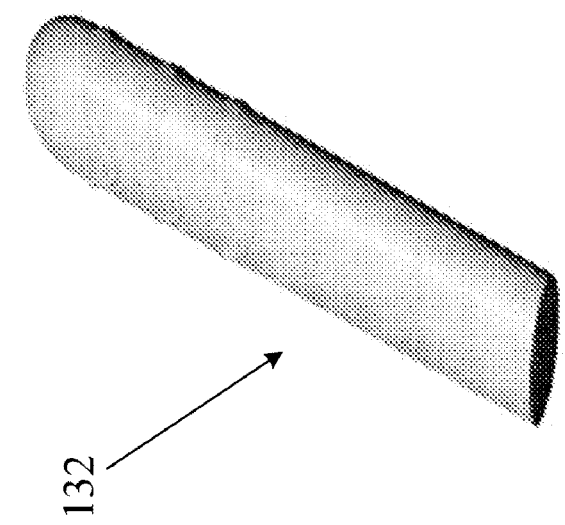

Examples of tampons with patterned impressions formed by a split cavity mold having patterns or pattern die elements oriented substantially or nearly perpendicular to the longitudinal axis of the compressed pledget or tampon are shown and described with respect to FIGS. 14-16. Examples of tampon patterns formed by mold having patterns or pattern die elements oriented substantially or nearly perpendicular to the longitudinal axis of a compressed pledget or tampon are shown and described with respect to FIGS. 17-21.

Accordingly, the compressed pledget 33, the compression machine cavity 60 in the compressed configuration, the mold cavity 68, and the compression member head 76, each may have cross-sectional shapes and dimensions which are very similar. These close tolerances may help avoid trapping of fibers from the compressed pledget 33 as the compression member head 76 transfers the compressed pledget into the mold cavity 60. Trapped fibers may create binding and shearing forces that may damage the tampon forming apparatus 32 or tear or otherwise damage the compressed pledget 33, or both. In certain embodiments, the compressed pledget 33, the compression machine cavity 60 in the compressed configuration, and the compression member head 76, each may have cross-sectional shapes and dimensions which are very dissimilar and, in certain embodiments, even substantially non-identical. In these instances, coordination between the compression member head 76 and the compression machine cavity 60 should be controlled to minimize or otherwise prevent damage to the tampon forming apparatus 30 or the compressed pledget 33, or both, when the compressed pledget 33 is removed from the compression machine cavity 60.

According to certain embodiments, the compressed pledget 33 may be heated in the mold cavity 68 to impart a self-sustaining shape to the compressed pledget 33 and resulting tampon. Methods of setting or stabilizing the tampon shape are well known and include heating the compressed pledget 33 with steam as disclosed in U.S. patent application Ser. No. 10/887,645 or thermal temperature gradient conduction or microwaving, as disclosed in U.S. Pat. No. 7,047,608.

A variety of materials may be used to make the components of the tampon forming apparatus 30. Suitable materials may be relatively rigid and include, but are not limited to stainless steel, and in the case of microwave heat stabilization, microwave safe materials.

C. Method of Making Tampons

Figure 10:
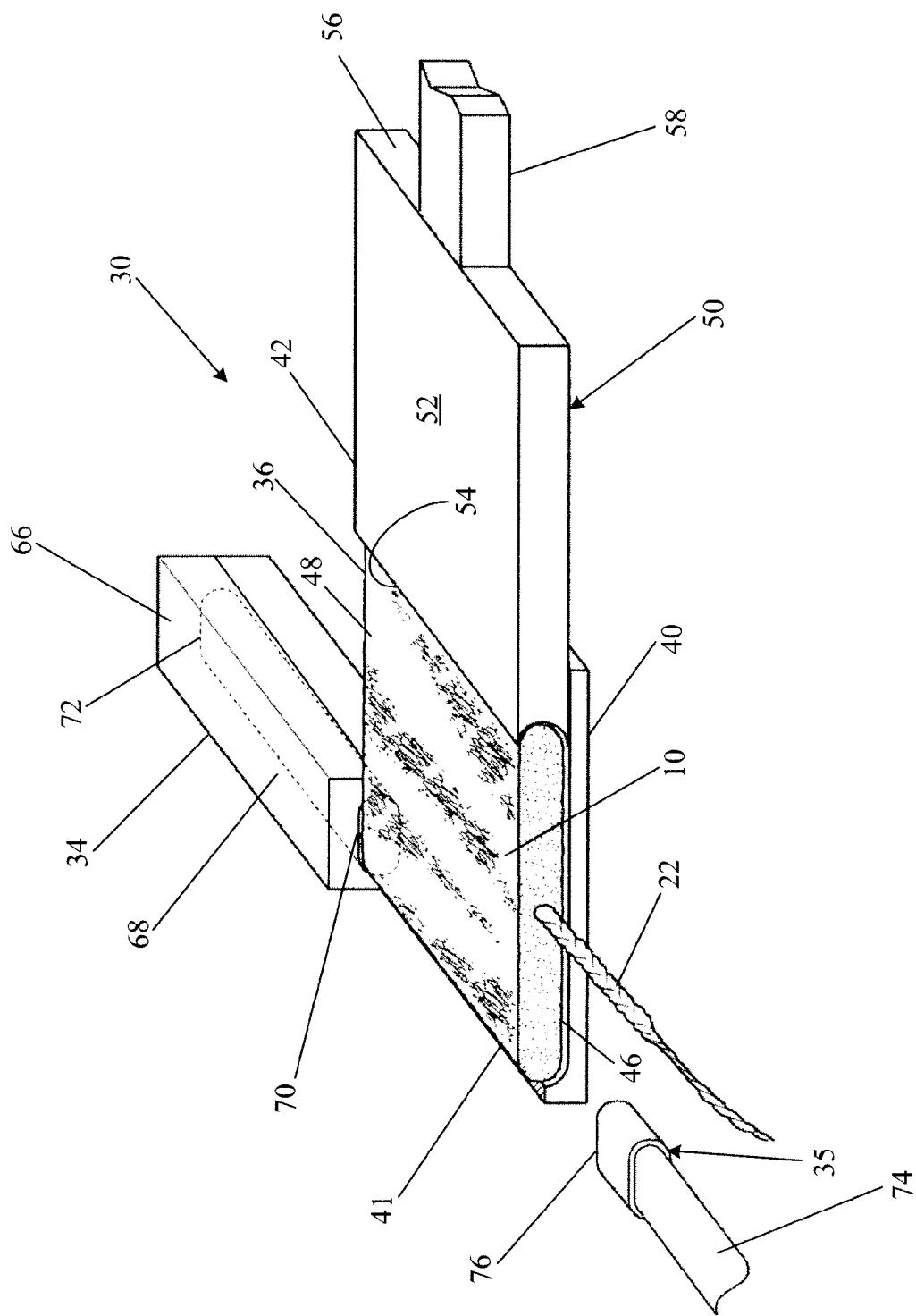
FIG. 10 is partial perspective view of the tampon forming apparatus in FIG. 2 with the tampon compression machine in open position and an uncompressed pledget in the tampon compression machine cavity.

A tampon may be made in accordance with an embodiment of this invention by first inserting the uncompressed pledget 10 in the open compression machine cavity 60 as shown in FIG. 10. As described hereinbefore, the thickness T1 of the uncompressed pledget 10 may be very close to the thickness T2 of the compression machine cavity 60 and the width W1 of the uncompressed pledget 10 may be close to or less than the width W2 of the compression machine cavity 60. The length L1 of the uncompressed pledget 10, however, may be less than the length L2 of the compression machine cavity 60.

According to certain embodiments, the thickness of the uncompressed pledget 10 can vary as can the particular dimensions of the compression machine cavity 60, mold cavity 68, and compression member head 76, but, according to certain embodiments, uncompressed pledget 10 thickness may generally range from about 5 to about 15 millimeters, or from about 5 to about 12 millimeters, or from about 5 to about 9.8 millimeters.

Figure 11:
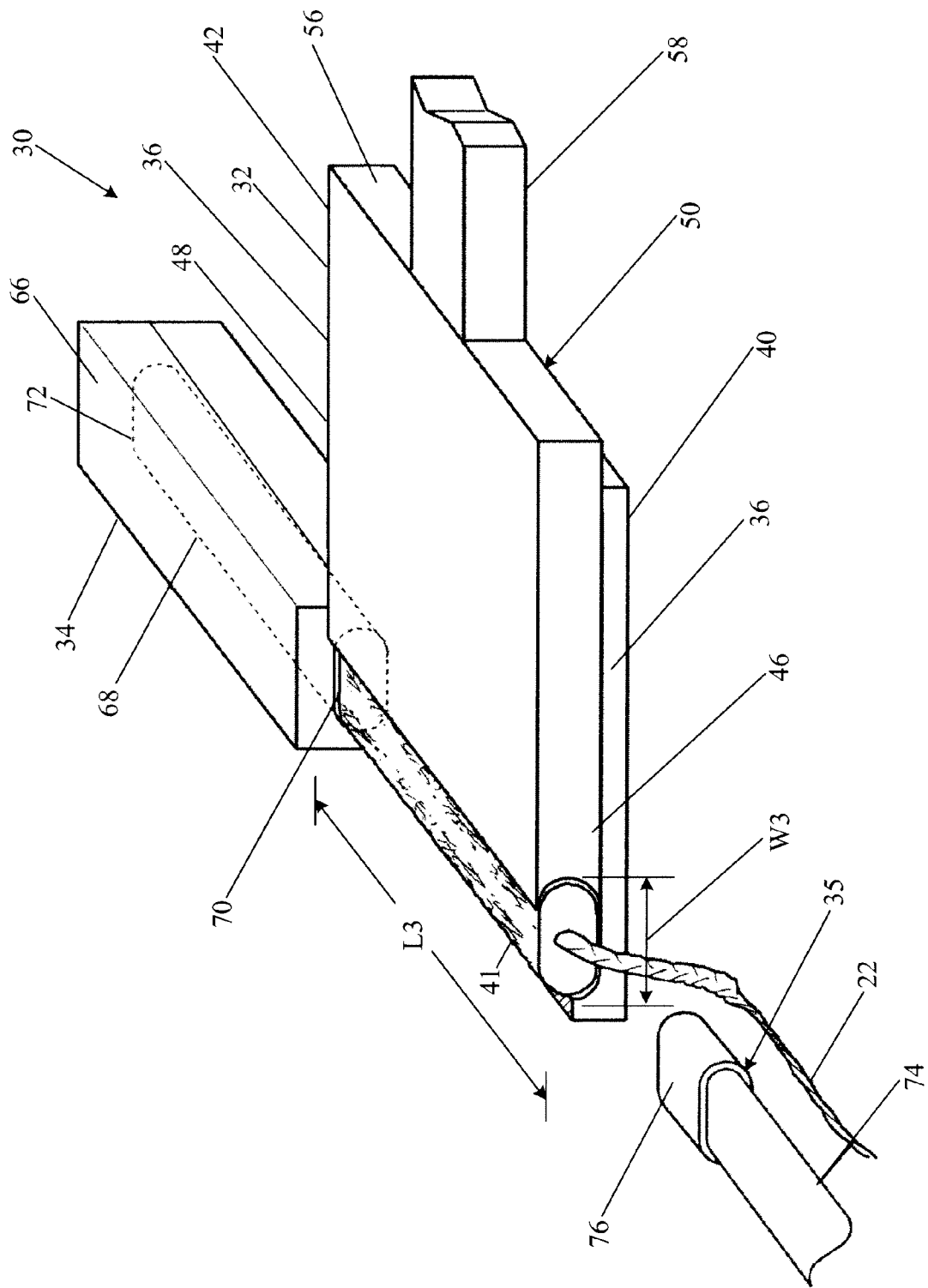
FIG. 11 is a partial perspective view of the tampon forming apparatus of FIG. 2 with the tampon compression machine in a final compression position and a compressed pledget in the compression machine cavity.

The uncompressed pledget 10 may then be compressed in the compression machine cavity 60 by actuating the die 50 of a tampon compression machine 32 within the anvil channel 44 toward the end wall 41 of the anvil 36 until the compressed configuration illustrated in FIGS. 4 and 11 is reached. The amount of force required to compress the pledget 10 may vary but suitable forces typically are about 50 to about 1000 psi. A variety of techniques for actuating the compression die 50 are well known and may include, but are not limited to a modified tampon compression machine available from Tory Engineering Company, of Osaka, Japan. According to certain embodiments, the compressed pledget width W3 is predetermined and the compression machine 32 compresses the uncompressed pledget 10 only to the compressed pledget width W3. In accordance with certain embodiments, methods for stopping the compression applied by the die 50 may include, but are not limited to a stop or détente structure for stopping forward movement of the die 50 when the predetermined compressed pledget width W3 is reached or suitable controls on the actuating mechanism for reciprocating the die 50.

After compression in the tampon compression machine 32, the compressed pledget 33 may be ejected from the compression machine cavity 60 by actuating the compression member 35 so that the compression member head 76 enters the inlet end 46 of the compression machine cavity and extends through the compression machine cavity 60 forcing the compressed pledget 33 through the inlet end 70 of the mold cavity 68.

Figure 12:
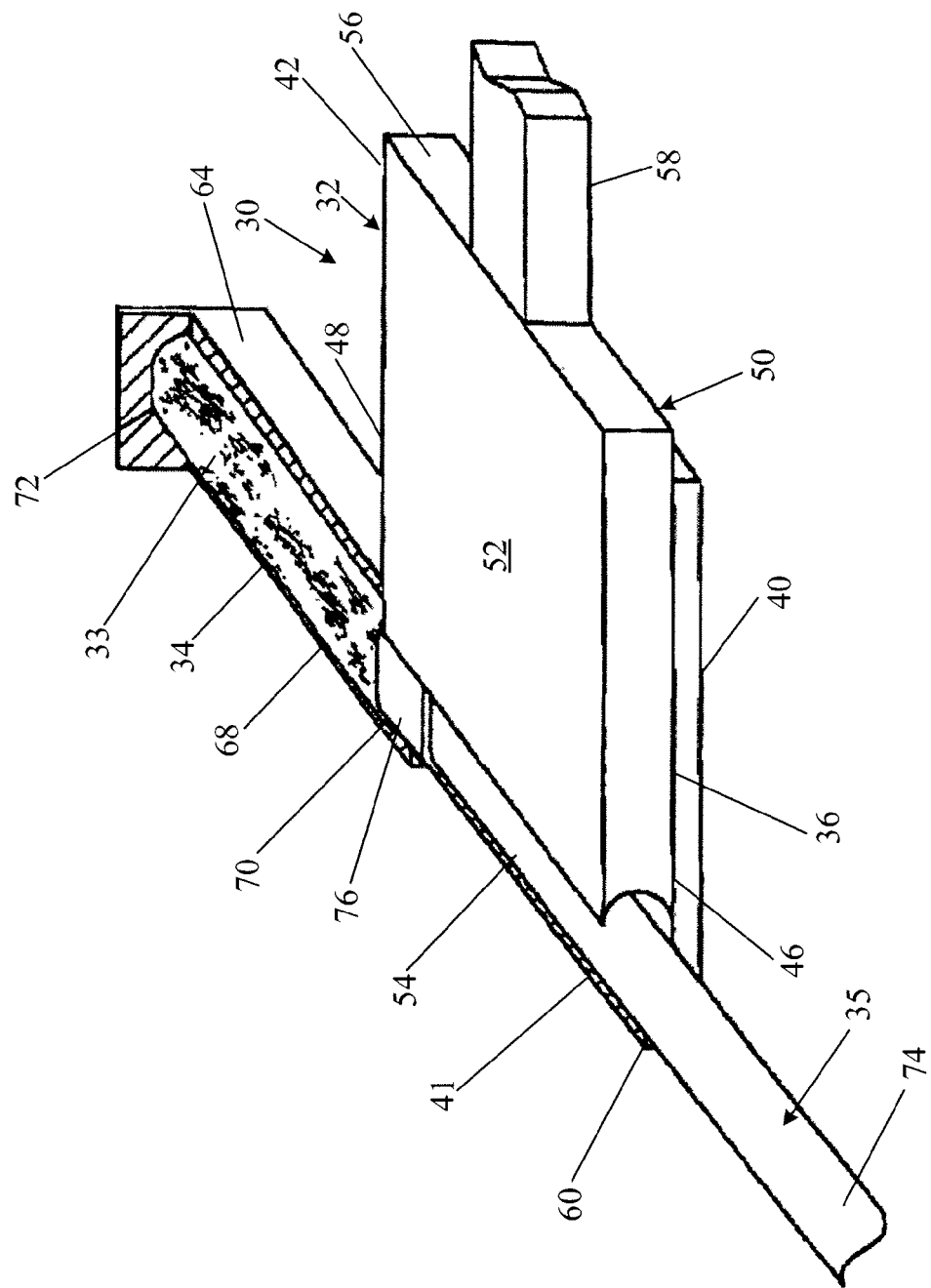
FIG. 12 is a partial perspective view of the tampon forming apparatus of FIG. 2 with a compressed pledget in the tampon split mold cavity.

When the compressed pledget 33 initially enters the mold cavity 68, the compressed pledget 33 may be forced into the mold cavity 68 until the compressed pledget 33 compacts against the distal end 72 of the mold cavity 68 and the compressed pledget 33 is completely within the mold cavity 68 as shown in FIG. 12.

Figure 13:
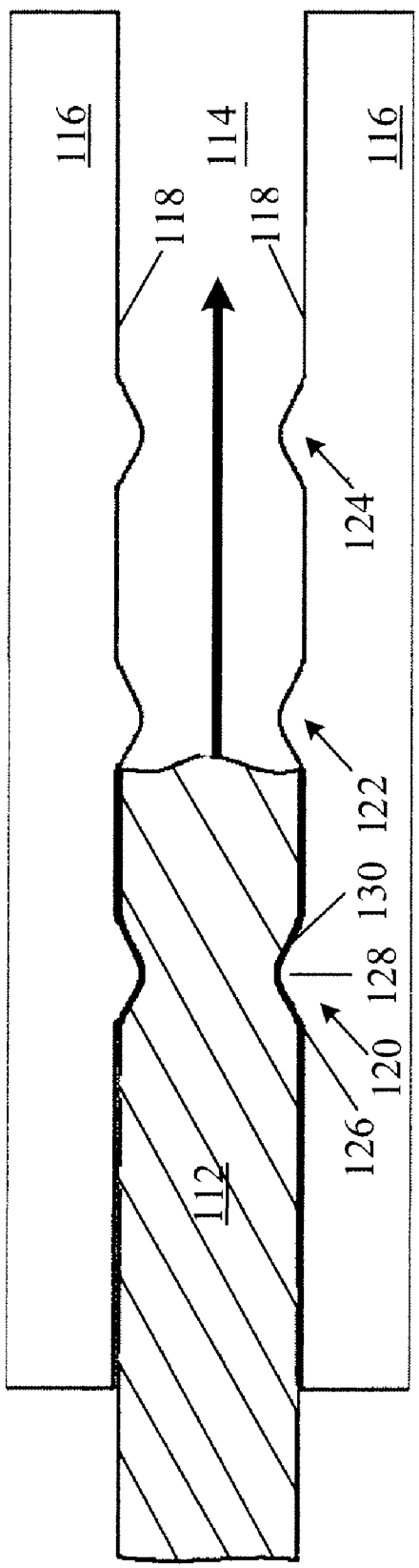
FIG. 13 is a detail view of a compressed pledget being forced into an example tampon split mold cavity in accordance with an embodiment of the invention.

FIG. 13 is a detail view of a compressed pledget being forced into an example tampon split mold cavity in accordance with an embodiment of the invention. In this example, a compressed pledget 112, similar to 33, is shown being introduced into a mold cavity 114, similar to 68, associated with a split cavity mold 116. The compressed pledget 112 may be forced along a base portion 118 of the mold cavity 114 and past one or more pattern die elements 120, 122, 124. When the external surface of the compressed pledget 112 encounters a lead in portion 126, similar to 88 in FIGS. 7-8, associated with pattern die elements 120, the pledget material may flow over the lead in portion 126 to a raised portion of the pattern die element 120. The relatively smooth slope of the lead in portion 126 may assist the pledget material in moving across the surface of the split cavity mold 116 between the base portion 118 and a raised portion 128 of the pattern die element 120 with minimal tearing or damage to the pledget material. The pledget material may then flow over the raised portion 128 of the pattern die element 120 to a trailing portion 130 of the pattern die element 120, and flow over the trailing portion 130 to the base portion 118 of the split cavity mold 116. The relatively smooth slope of the trailing portion 130 may assist the pledget material in moving across the surface of the split cavity mold 116 between the raised portion 128 and the base portion 118 with minimal or no tearing or damage to the pledget material. In this manner, a compressed pledget may be introduced into and pushed through the split cavity mold to facilitate formation of various pattern impressions which may be oriented substantially or nearly perpendicular to the longitudinal axis of the compressed pledget with minimal or no tearing or damage to the pledget material or compressed pledget.

Generally, the compressed pledget 33 may be compressed by the tampon compression machine 32 to a predefined size depending on the patterns or pattern die elements associated with the mold 34. In certain embodiments for forming convex-shaped pattern impressions on a tampon, the compressed pledget 33 may be compressed to match or approximate the smallest diameter of the mold cavity 68 or 114. When the compressed pledget 33 is forced into the mold cavity 68 or 114, the compressed pledget may expand slightly to fill the concave-shaped pattern die elements associated with the mold 34. In certain embodiments for forming concave-shaped pattern impressions on a tampon, the compressed pledget 33 may be compressed to match or approximate the smallest diameter of the mold cavity 68 or 114. When the compressed pledget 33 is forced into the mold cavity 68 or 114, the compressed pledget may move over the lead in portions and trailing portions of the convex-shaped pattern die elements associated with the mold 34. In certain embodiments for forming offset patterned impressions on opposing lateral sides of a tampon, such as offset convex-shaped patterned impressions, the compressed pledget 33 may be compressed to match or approximate the largest diameter of the mold cavity 68 or 114. That is, the diameter of the mold cavity at a point which includes only one pattern die element. In certain tampon embodiments with offset concave-shaped patterned impressions on opposing lateral sides of a tampon, the compressed pledget 33 may be compressed to match or approximate the smallest diameter of the mold cavity 68 or 114.

In one embodiment, the compression member head 76 may include one or more patterns or pattern die elements, such that when the compression member head 76 forces the compressed pledget into the mold cavity 68 or 114, a pattern impression corresponding to the one or more patterns or pattern die elements may be formed adjacent to an end of the compressed pledget.

In another embodiment, the compression member head 76 may provide a suitable amount of compression on the compressed pledget within the mold cavity 68 or 114 to force the opposing end of the compressed pledget into a mold with one or more patterns or pattern die elements adjacent to the opposing end of the compressed pledget. In certain embodiments, pattern impressions such as a tapered tip or blunt tip can be formed at an opposing end of the compressed pledget. In other embodiments, pattern impressions such as raindrop-shaped elements crossing over from one lateral side to another lateral side of the compressed pledget can be formed adjacent to the opposing end of the compressed pledget.

In any instance, once in the mold cavity 68, the compressed pledget 33 may be stabilized by conventional heat treatment and then ejected from the mold cavity by conventional means such as by pulling the withdrawal cord 22, manually or mechanically by pushing, grasping, hooking, picking, or clamping the tampon and withdrawing it from the mold, or vacuum withdrawal, or the like. Suitable methods of tampon removal from the mold are described in U.S. Pat. No. 7,047,608.

D. Tampons

Tampons made by the foregoing method may have patterned impressions which may be substantially or nearly perpendicular to a longitudinal axis of the tampon created in the outer surface of the tampon. In certain embodiments, tampons made in accordance with the foregoing method may have a width to thickness ratio of approximately 1.0:1.0 to approximately 1.8:1.0.

Example tampons and tampon patterns made in accordance with embodiments of this invention are illustrated in FIGS. 14-21. The tampon 132 illustrated in FIG. 14 is made according to an embodiment of this invention and may have a plurality of patterned impressions along the exterior surface of the tampon 132. In this embodiment, the patterned impressions may be a series of three convex, chevron-shaped rib elements, which may be generally perpendicular to a longitudinal axis of the tampon 132. In certain embodiments, the patterned impressions may be approximately 0.5 mm in height above or below the exterior surface of the tampon, for instance, a patterned impression can be a convex-shaped element approximately 0.5 mm in height above the exterior surface of the tampon.

Figure 21:
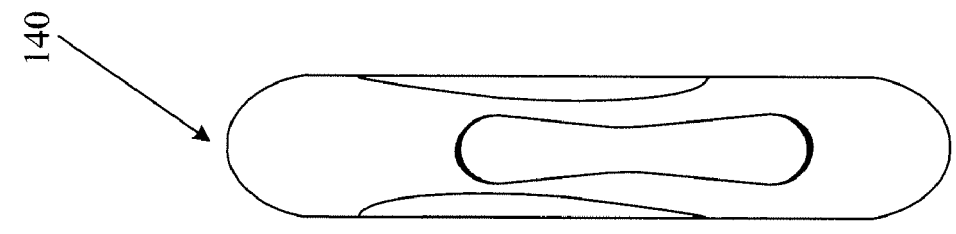
FIGS. 17-21 are perspective views of example tampon patterns made in accordance with various embodiments of this invention.
Figure 20:
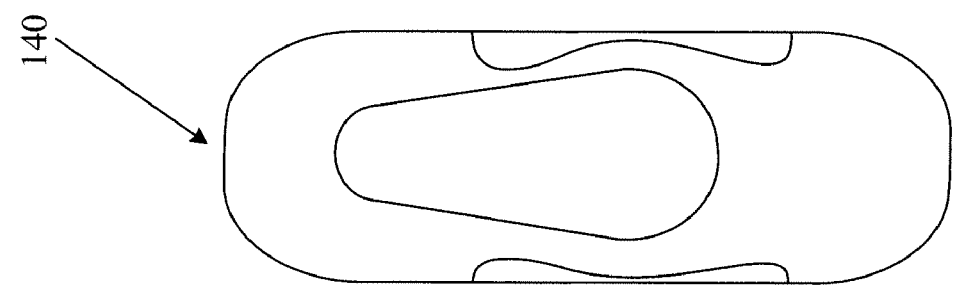
Figure 19:
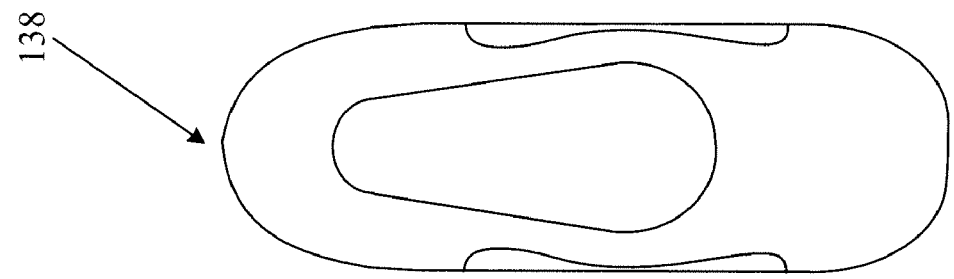
Figure 18:
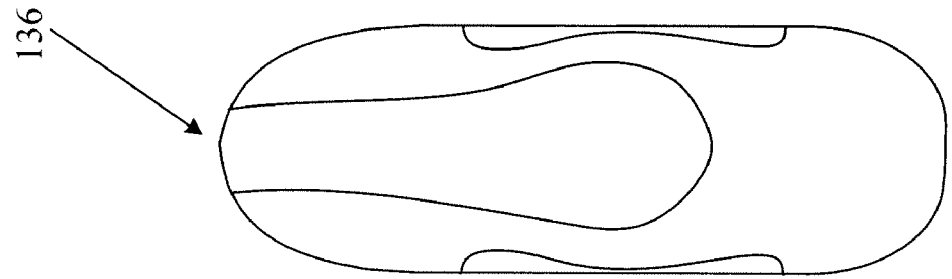
Figure 17:
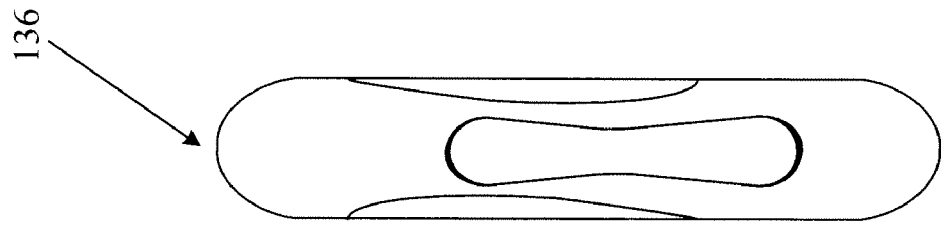

The tampon 132 as illustrated in FIG. 14, the tampon 134 in FIGS. 15 and 16, the tampon pattern 136 in FIGS. 17 and 18, the tampon pattern 138 in FIG. 19, the tampon pattern 140 in FIGS. 20 and 21, and the tampons and tampon patterns made according to embodiments of this invention can be made by applying a compression to the uncompressed pledget 10, shown in FIG. 1, and forcing the compressed pledget 33 into a mold cavity, wherein the mold cavity comprises at least one pattern oriented substantially perpendicular to the longitudinal axis of the compressed pledget, wherein the at least one pattern comprises at least one smooth lead in portion associated with one or more design elements. This is explained in detail in the foregoing description of the tampon forming apparatus 30. Prior art processes which manufacture tampons by applying compression to a compressed pledget within a mold cavity with generally longitudinally-oriented patterns are distinct from the process of this invention.

In the embodiment of a tampon shown in FIGS. 15 and 16, the tampon 134 may have patterned impressions on opposing lateral sides including three concave, chevron-shaped rib elements, which may be generally perpendicular to a longitudinal axis of the tampon 134. As shown in this example, the patterned impressions on one lateral side of the tampon 134 may be offset from similar shaped pattern impression on an opposing or another lateral side of the tampon 134. In certain embodiments, the patterned impressions may be approximately 0.5 mm in height above or below the exterior surface of the tampon.

In the embodiment of a tampon pattern shown in FIGS. 17-18, a tapered tip tampon having a pattern such as 136 may have patterned impressions on four lateral sides of the tampon including concave, peanut-shaped elements on the relatively thinner lateral sides and the concave, and open raindrop-shaped elements on the relatively wider lateral sides, wherein the open raindrop-shaped elements cross over the upper portion or top of the tampon. Some or all of the peanut-shaped and raindrop-shaped elements may have portions that are generally perpendicular to a longitudinal axis of the associated tampon. In certain embodiments, the patterned impressions may be approximately 0.5 mm in height above or below the exterior surface of the associated tampon, and may decrease to approximately 0.25 mm in height above or below the exterior surface of the tampon as the elements cross over the upper portion or top of the tampon.

In the embodiment of a tampon pattern shown in FIG. 19, a tapered tip tampon having a tampon pattern such as 138 may have patterned impressions on four lateral sides of the tampon, including concave, peanut-shaped elements on the relatively thinner lateral sides and the concave, raindrop-shaped element on the relatively wider lateral sides, wherein some or all of the elements may have portions that are generally perpendicular to a longitudinal axis of the tampon. In certain embodiments, the patterned impressions may be approximately 0.5 mm in height above or below the exterior surface of the associated tampon, and may decrease to approximately 0.25 mm in height above or below the exterior surface of the tampon towards the upper portion or top of the tampon.

In the embodiment of a tampon pattern shown in FIGS. 20-21, a blunt tip tampon having a tampon pattern such as 140 may have patterned impressions on four lateral sides of the tampon, including concave, peanut-shaped elements on the relatively thinner lateral sides and the concave, raindrop-shaped element on the relatively wider lateral sides, wherein some or all of the elements may have portions that are generally perpendicular to a longitudinal axis of the tampon. In certain embodiments, the patterned impressions may be approximately 1.0 mm in height above or below the exterior surface of the associated tampon, and may decrease to approximately 0.5 mm in height above or below the exterior surface of the tampon towards the upper portion or top of the tampon.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:

1. A method for making a tampon comprising:
    providing an uncompressed pledget of absorbent material;
    compressing the uncompressed pledget in a compression machine;
    feeding the compressed pledget with a compression member into a tampon mold having a mold cavity for receiving the compressed pledget of absorbent material, wherein the mold cavity comprises at least one pattern oriented substantially perpendicular to the longitudinal axis of the compressed pledget, wherein the at least one pattern comprises:
        one or more design elements,
        at least one smooth, sloped lead in portion, and
        at least one smooth, sloped trailing portion associated with the one or more design elements; and
    molding the compressed pledget into a tampon having an exterior surface, the exterior surface comprising at least one patterned impression oriented substantially perpendicular to the longitudinal axis of the tampon, wherein the patterned impression corresponds to the at least one pattern of the mold cavity.

2. The method of claim 1, further comprising:
    stabilizing the compressed pledget, wherein at least one pattern impression corresponding to the at least one pattern remains on the formed tampon.

3. The method of claim 1, wherein compressing the uncompressed pledget in a compression machine comprises compressing the uncompressed pledget to approximately the maximum or minimum internal diameter of the tampon mold.

4. The method of claim 1, wherein feeding the compressed pledget with a compression member into a tampon mold comprises pushing the compressed pledget over the at least one smooth lead in portion or trailing portion associated with one or more design elements.

5. The method of claim 1, wherein the one or more design elements comprise at least one of the following: a concave-shape, a convex-shape, a combination concave and convex shape, lines, chevrons, rain drops, peanuts, dimples, concentric circles, cross-hatching, stars, polygons, triangles, rings, rectangles, petals, ellipsoids, tear drops, letters, or waves.

6. The method of claim 1, wherein the one or more design elements comprise offset design elements on opposing sides of the mold cavity.

* * * * *